(12) United States Patent
Nakahara et al.

(10) Patent No.: US 6,733,785 B1
(45) Date of Patent: May 11, 2004

(54) MOISTURE-SENSITIVE PREPARATION OF PERCUTANEOUS ABSORPTION TYPE

(75) Inventors: Kaname Nakahara, Saitama (JP); Toshinobu Seki, Saitama (JP)

(73) Assignees: Lintec Corporation, Tokyo (JP); Research Institute of TTS Technology, Tokyo (JP); Toko Pharmaceutical Ind. Co., Ltd., Tokyo (JP)

( * ) Notice: Subject to any disclaimer, the term of this patent is extended or adjusted under 35 U.S.C. 154(b) by 0 days.

(21) Appl. No.: 09/762,615

(22) PCT Filed: Jun. 9, 2000

(86) PCT No.: PCT/JP00/03782

§ 371 (c)(1),
(2), (4) Date: Feb. 8, 2001

(87) PCT Pub. No.: WO00/76485

PCT Pub. Date: Dec. 21, 2000

(30) Foreign Application Priority Data

Jun. 11, 1999 (JP) ............................... 11/165693

(51) Int. Cl.[7] ............................. A61K 9/14; A61K 9/00; A61F 13/02
(52) U.S. Cl. ..................... 424/484; 424/400; 424/486; 424/487; 424/448
(58) Field of Search .................................. 424/402, 443, 424/449

(56) References Cited

U.S. PATENT DOCUMENTS

| 3,645,835 | A | * | 2/1972 | Hodgson | 161/146 |
| 5,176,916 | A | * | 1/1993 | Yamanaka et al. | 424/448 |
| 5,232,702 | A | * | 8/1993 | Pfister et al. | 424/448 |
| 5,446,070 | A | * | 8/1995 | Mantelle | 514/772.6 |
| 5,662,926 | A | * | 9/1997 | Wick et al. | |

FOREIGN PATENT DOCUMENTS

| JP | 61-078720 | 4/1986 | A61K/9/70 |
| JP | 2-149514 | 6/1990 | A61K/9/70 |

* cited by examiner

Primary Examiner—Thurman K. Page
Assistant Examiner—Humera N. Sheikh
(74) Attorney, Agent, or Firm—Oblon, Spivak, McClelland, Maier & Neustadt, P.C.

(57) ABSTRACT

The invention relates to a percutaneous absorption preparation which comprises a supporting body, a medicine storage layer, a permeation controlling film, a layer of an adhesive and a release liner and which is featured in that the above-mentioned permeation controlling film is plasticized by moisture volatilized from the skin at the time of application of the preparation.

11 Claims, 2 Drawing Sheets

MOISTURE-SENSITIVE PREPARATION OF PERCUTANEOUS ABSORPTION TYPE

TECHNICAL FIELD

The present invention relates to a percutaneous absorption preparation, more particularly to a reservoir type percutaneous absorption preparation wherein at the time of preservation a permeation controlling film is in-permeable to medicines and the medicines exist stably in a medicine storage layer and wherein at the time of application of the preparation, as the permeation controlling film is plasticized by moisture evaporating from the skin, the medicines move into a layer of an adhesive and are absorbed through the skin.

BACKGROUND ART

As a conventional percutaneous absorption preparation there is reported a system in which a medicine storage layer and a medicine activating agent are divided by a medicine in-permeable film and, with the in-permeable film being made destroyed or burst by the user upon application, the medicine moves to a layer of an adhesive by the aid of the activating agent and is absorbed through the skin(JP-A-H1-85912). This system, however, leads to lowered compliance of the patient side because it needs the work of the destroying or bursting the user has to do upon application, and moreover has the defect that the manufacturing method is complicated. Further, the system poses the problem in the case of a patch preparation in which the medicine is contained in the layer of an adhesive, in that it lacks long-term preservability and introduces the lowering of the medicine content or eventually reduced therapeutic effect because the medicine gradually decomposes or deteriorates if the medicine is an unstable compound in the layer of an adhesive.

DISCLOSURE OF THE INVENTION

The object of the present invention is to provide a percutaneous absorption preparation which is simple in its use and manufacturing method, and which, even when the medicine is an unstable compound in the layer of an adhesive, makes the medicine preservative stably by restraining its decomposition and deterioration during preservation and which allows the medicine to move to the layer of adhesive and the skin and to be absorbed through the skin at the time of application of the preparation.

The inventors studied earnestly to solve the above problem and found as a result that the problem concerned was solved by the percutaneous absorption preparation which comprised a supporting body, a medicine storage layer, a permeation controlling film, a layer of an adhesive and a release liner and which was featured in that the above permeation controlling film was plasticized by moisture volatilized from the skin upon application of that preparation, thus achieving the present invention.

Namely, the present invention includes the following inventions.
(1) A percutaneous absorption preparation comprising a supporting body, a medicine storage layer, a permeation controlling film, a layer of an adhesive and a release liner, which is characterized in that the permeation controlling film is plasticized by moisture volatilized from the skin at the time of application of the preparation.
(2) A percutaneous absorption preparation according to the above (1), wherein the permeation controlling film is a water-soluble polymer.
(3) A percutaneous absorption preparation according to the above (2), wherein the water-soluble polymer is poly(vinyl alcohol).
(4) A percutaneous absorption preparation according to the above (1), wherein the medicine storage layer is formed by a medicine, or a medicine and a vehicle.
(5) A percutaneous absorption preparation according to the above (4), wherein the medicine is water-soluble.
(6) A percutaneous absorption preparation according the above (4), wherein the vehicle is a water-disintegrative substance.
(7) A percutaneous absorption preparation according to the above (1), wherein the supporting body has a water-vapor permeability of 100 $g/m^2$ or less at the condition of 40° C. and 24 hours.
(8) A percutaneous absorption preparation according to the above (1), wherein the adhesive has a water-vapor permeability of 100 $g/m^2$ or more at the condition of 40° C. and 24 hours.
(9) A percutaneous absorption preparation according to the above (1), wherein the therapeutic medicine is nicorandil, dopamine hydrochloride or eperisone hydrochloride.

The present invention is explained in detail in the following.

The percutaneous absorption preparation of the present invention is one which comprises a supporting body, a medicine storage layer, a permeation controlling film, a layer of an adhesive and a release liner and which is characterized in that the above-mentioned permeation controlling film is plasticized by moisture evaporating from the skin at the time of application of the preparation.

The word "plasticize" means "to make a substance prone to cause plastic deformation or plastic flow by an external force", and in the case of the invention it means that the permeation controlling film gives rise to plastic flow because of its absorbing moisture and the medicine activated by moisture permeates, dissolves, disperses or diffuses into the permeation controlling film.

In the percutaneous absorption preparation of the present invention, it is necessary that the permeation controlling film is located between the medicine storage layer and the layer of adhesive and plasticized by moisture volatilized from the skin upon application of the preparation. Thus, the medicine, or the medicine and vehicle permeates, dissolves, disperses or diffuses into the permeation controlling film and moves to the layer of adhesive, and the medicine is absorbed through the skin. As the permeation controlling film any component may be used without limitation as long as it is plasticized by moisture evaporating from the skin and allows the permeation of the medicine when the preparation is applied. As such permeation controlling films there are enumerated water-soluble polymers, preferably synthetic polymers such as poly(vinyl alcohol) and poly(vinylpyrrolidone), polysaccharides such as soluble starch, dextrin, cellulose, methylcellulose and carboxymethylcellulose, natural polymers such as corn starch, sodium alginate, gum arabic, gelatin and pullulan, and inorganic polymers such as sodium polyphosphate and water glass. Most preferred is poly(vinyl alcohol).

In the percutaneous absorption preparation of the present invention, the medicine storage layer is formed by a medicine, or a medicine and a vehicle (excipient).

As the vehicle preferably enumerated are water-disintegrative substances, though there is no limitation as long as it is ones generally used. Here, "water-disintegrative substance" indicates "a substance which functions as a vehicle at the time of preparing the medicine storage layer and as a disintegrative agent in the presence of moisture at the time of applying the preparation." Such water-disintegrative substances include, for example, saccharides such as glucose, lactose, sucrose, starch, soluble starch and methylcellulose, polyethyleneglycols and polysolbates.

As the therapeutic medicine used for the medicine storage layer, any may be employed without limitation as long as it is absorbed percutaneously. Preferable are amine type therapeutic medicines such as nicorandil, dopamine hydrochloride and eperisone hydrochloride.

Further, as the therapeutic medicine there are enumerated non-steroidal anti-inflammatory drugs, steroid type anti-inflammatory drugs, antiarrhythmic drugs, antitumor agents, hypnotics, psychotropic drugs, local anesthetic drugs, cardiotonic drugs, antibiotics, antituberculosis drugs, analgesic agents, muscular relaxants, anti-asthma drugs, anti-cholinergic agents, vasodilators, antihypertensive agents, antihistamines, cholinergic agents and angiotensin invertase inhibitors.

It is needed that the therapeutic medicine used in the percutaneous absorption preparation of the present invention permeates, dissolves, disperses or diffuses into the permeation controlling film that has been plasticized by moisture volatilized from the skin.

The medicine storage layer may incorporate, if necessary, additives such as kaolin, talc, bentonite, titanium oxide, calcium bicarbonate, aluminum sulfate, silicic anhydride, zinc oxide, silica and alumina; antioxidants such as BHT, BHA, guaiacol ester and nordihydroguaiaretic acid; and absorption accelerators such as crotamiton, benzyl alcohol, ethanol, diethyl sebacate and isopropyl myristate.

To retain the medicine storage layer in the percutaneous absorption preparation of the present invention, the upper part or outside of the medicine-storage layer is needed to be covered by a supporting body.

Although the supporting body in the percutaneous absorption preparation of the present invention is not limited to a particular material as long as it is in-permeable to the medicine and water-vapor, preferred is one that has a water-vapor permeability of 100 g/m$^2$ or less after 24 hours at 40° C. (determined according to JIS Z0208,Testing Method of Water-vapor Permeability of Moisture-proof Packaging Material (Cup Method)). Examples of such supporting body include a sheet and a film of poly(ethylene terephthalate), polyethylene and polypropylene, a laminated sheet made by using two or more of the above and a laminated sheet of the above film and sheet with a nonwoven fabric or woven fabric.

The adhesive in the percutaneous absorption preparation of the present invention is not limited to a particular component as long as it is attachable to the skin and permeable to water-vapor, but preferable is such that has a water-vapor permeability of 100 g/m$^2$ or more after 24 hours at 40° C. As such adhesives there are enumerated, for example, acrylic adhesives, rubber type adhesives and silicone type adhesives. The layer of adhesive may incorporate, other than the above adhesives, according to necessity, adhesion providing agents such as rosin resin, terpene resin, aromatic hydrocarbon resin, aliphatic hydrocarbon resin, petroleum resin, ester gum, fat-like phenol resin; softening agents such as isopropyl myristate, oleyl oleate, polybutene, isopolybutene, liquid paraffin, squalene, silicone oil, olive oil, soybean oil, rape seed oil, coconut oil and beef tallow; additives such as kaolin, talc, bentonite, titanium oxide, calcium bicarbonate, aluminum sulfate, silicic anhydride, zinc oxide, silica and alumina; antioxidants such as BHT, BHA, guaiacol ester and nordihydroguaiaretic acid; and absorption assistants such a scrotamiton, benzyl alcohol, ethanol, diethyl sebacate and isopropyl myristate.

The release liner in the percutaneous absorption preparation of the present invention is not limited particularly as long as it is a material soft and in-permeable to the medicine and is exemplified by a film of polyethylene, polyester and the like which is coated with a silicone resin as releasing agent.

One mode of the percutaneous absorption preparation of the present invention can be illustrated by what has the structures shown in FIGS. 1(A) and (B).

In FIGS. 1(A) and (B), the numeral 1 denotes a supporting body, 2 a medicine storage layer, 3 a permeation controlling film, 4 a layer of adhesive and 5 denotes a release liner.

In the percutaneous absorption preparation shown in FIG. 1, supporting body 1 is located on the upper part or outside of medicine storage layer 2 and performs the function of retaining medicine storage layer 2. Permeation controlling film 3 is located on the lower part of medicine storage layer 2 and takes the function of controlling the permeation of the medicine into the layer of adhesive 4. The layer of adhesive 4 is located on the lower part of permeation controlling film 3 and performs the function of affixing the patch preparation to the skin. Upon using the patch preparation, release liner 5 located on the lower part of the layer of adhesive 4 is removed and the preparation is applied to the skin.

The medicine contained in medicine storage layer 2 is absorbed through the skin via permeation controlling film 3 and layer adhesive 4.

This is specification includes part or all of the contents as disclosed in the specification of Japanese Patent Application No. 11(1999)-165693, which is a base of priority claim of the present application.

BRIEF DESCRIPTION OF DRAWINGS

1 . . . supporting body
2 . . . medicine storage layer
3 . . . permeation controlling film
4 . . . layer of adhesive
5 . . . release liner

BEST MODE FOR CARRYING OUT THE INVENTION

Figure 1:
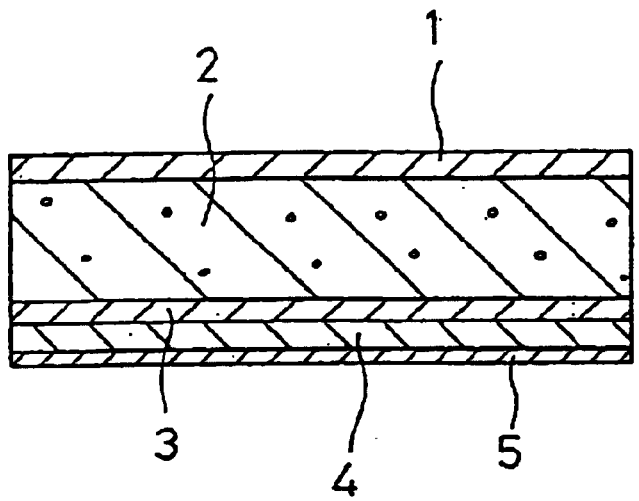
FIG. 1 is a sectional view of the percutaneous absorption preparation of the present invention. The numbers in the figure denote the following.
Figure 1:
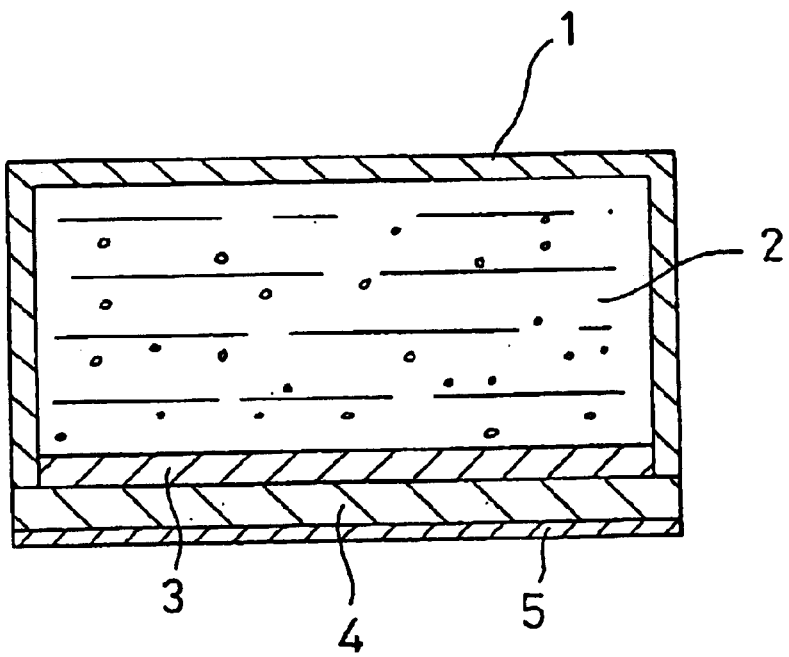

Hereinafter the present invention is explained in detail by way of Examples and Comparative Examples, which, however, should not be considered as limiting the scope of the present invention.

EXAMPLE 1

To 100 parts by weight of an acrylic adhesive (PE-300, made by Nippon Carbide Ind.) there was added 4.0 parts by weight of a crosslinking agent (CK-101, made by Nippon Carbide Ind.), and ethyl acetate was added so as for the weight of the solids per the total weight to make 40% by weight. The mixture was fully stirred with a Disper to prepare a uniform solution. This solution was coated uniformly on a release film comprising a 38 μm thick poly (ethylene terephthalate) film and dried for 4 minutes in a drying oven of 80° C. to form a layer of adhesive having a coating amount of 50 g/m$^2$. Then, a poly (vinyl alcohol) film having a thickness of 25 μm which was to make the permeation controlling film was affixed on the layer of adhesive.

Nicorandil of 10 parts by weight was dissolved in 90 parts by weight of methanol to prepare a solution having a nicorandil concentration of 10% (w/w). This solution was coated uniformly on a 50 μm thick poly (ethylene terephthalate) film and dried for 1 minute in a drying oven of 60° C., and the medicine storage layer was formed so as for the content of nicorandil to become about 300 mg/M².

This film was attached to the previously prepared poly (vinyl alcohol) film, layer of adhesive and release liner to produce a percutaneous absorption preparation.

EXAMPLE 2

A percutaneous absorption preparation was produced in the same manner as Example 1 except that preparation was made so that the coating amount of nicorandil may become about 600 mg/m² in contrast to about 300 mg/m² in the preparation of the medicine storage layer of Example 1.

EXAMPLE 3

The preparation of the medicine storage layer mentioned in Example 1 was conducted as in the following. To 100 parts by weight of purified water 4 parts by weight of soluble starch was dissolved as a vehicle, then 20 parts by weight of nicorandil was added and therein added was 300 parts by weight of ethanol, and the mixture was stirred. This liquid was uniformly coated on a poly(ethylene terephthalate) film and dried for 3 minutes in a drying oven of 110° C. to form a medicine storage layer. Except for this operation, the same operation as in Example 1 was performed to prepare a percutaneous absorption preparation so that the content of nicorandil thereof might become about 300 mg/m².

EXAMPLE 4

Except for using eperisone hydrochloride in place of nicorandil used in Example 1, the operation was conducted in the same manner as Example 1, and a percutaneous absorption preparation was prepared so that the content of eperisone hydrochloride might be about 300 mg/m².

EXAMPLE 5

Except for using dopamine hydrochloride in place of nicorandil used in Example 1, the operation was conducted in the same manner as Example 1, and a percutaneous absorption preparation was prepared so that the content of dopamine hydrochloride might be about 300 mg/m².

EXAMPLE 6

The preparation of the medicine storage layer mentioned in Example 1 was carried out as in the following. Twenty parts by weight of nicorandil and 80 parts by weight of soluble starch as a vehicle were mixed and dispersed, and the mixture was coated uniformly on a permeation controlling film. Except for this operation the same operation as in Example 1 was conducted to prepare a percutaneous absorption preparation in which the content of nicorandil was so made as to be about 300 mg/M².

COMPARATIVE EXAMPLE 1

To 100 parts by weight of an acrylic adhesive (PE-300, made by Nippon Carbide Ind.) there was added 4.0 parts by weight of a crosslinking agent (CK-101, made by Nippon Carbide Ind.) and 0.27 part by weight of nicorandil, and ethyl acetate was added so as for the weight of the solids per the total weight to make 40% by weight. The mixture was fully stirred with a Disper to prepare a uniform solution. This solution was coated uniformly on a release film comprising a 38 μm thick poly(ethylene terephthalate) film and dried for 4 minutes in a drying oven of 80° C. to form a layer of adhesive having a coating amount of 50 g/m² and a nicorandil content of about 300 mg/m². Then, a poly(ethylene terephthalate) film having a thickness of 50 μm was affixed to prepare a percutaneous absorption preparation.

COMPARATIVE EXAMPLE 2

Except for using eperisone hydrochloride in place of nicorandil used in Comparative Example 1, the operation was conducted in the same manner as Comparative Example 1, and a percutaneous absorption preparation was prepared so that the content of eperisone hydrochloride might make about 300 mg/m².

COMPARATIVE EXAMPLE 3

Except for using dopamine hydrochloride in place of nicorandil used in Comparative Example 1, the operation was conducted in the same manner as Comparative Example 1, and a percutaneous absorption preparation was prepared so that the content of dopamine hydrochloride might make about 300 mg/².

TEST EXAMPLE 1

The percutaneous absorption preparations obtained in Examples 1–6 and Comparative Examples 1–3 and having the compositions shown in Table 1 were cut into pieces of 25 mm×150 mm, wrapped in a packing material of aluminum and preserved for 8 weeks in a constant temperature bath of 23° C. (humidity 65%) regarding Examples 1–3, 6 and Comparative Example 1, or for 7 days in a constant temperature bath of 40° C. (dry) regarding Examples 4–5 and Comparative Examples 2–3. Then the amounts of the residual medicine in the preparations were determined with a HPLC. The results of the test on stability with time lapse were shown in Table 2.

TABLE 1

|  | Example | | | | | | Comparative Example | | |
|---|---|---|---|---|---|---|---|---|---|
|  | 1 | 2 | 3 | 4 | 5 | 6 | 1 | 2 | 3 |
| Permeation controlling film | ○ | ○ | ○ | ○ | ○ | ○ |  |  |  |
| Vehicle (Excipient) |  |  | ○ |  |  | ○ |  |  |  |
| Ingredient contained in medicine storage layer (ratio by weight) |  |  |  |  |  |  |  |  |  |
| Nicorandil | 1 | 2 | 1 |  |  | 1 | 1 |  |  |
| Eperisone hydrochloride |  |  |  | 1 |  |  |  | 1 |  |
| Dopamine hydrochloride |  |  |  |  | 1 |  |  |  | 1 |

TABLE 2

| | Rate of residual medicine (%) | |
|---|---|---|
| | 40° C. × 7 days | 23° C. × 8 weeks |
| Example | | |
| 1 | — | 99.27 |
| 2 | — | 98.78 |
| 3 | — | 99.01 |

TABLE 2-continued

| | Rate of residual medicine (%) | |
|---|---|---|
| | 40° C. × 7 days | 23° C. × 8 weeks |
| 4 | 99.90 | — |
| 5 | 99.89 | — |
| 6 | — | 99.30 |
| Comparative Example | | |
| 1 | — | 12.24 |
| 2 | 84.30 | — |
| 3 | 79.95 | — |

TEST EXAMPLE 2

Using the percutaneous absorption preparations obtained in Examples 1–3, the percutaneous absorbability was evaluated according to the following method.

Figure 2:
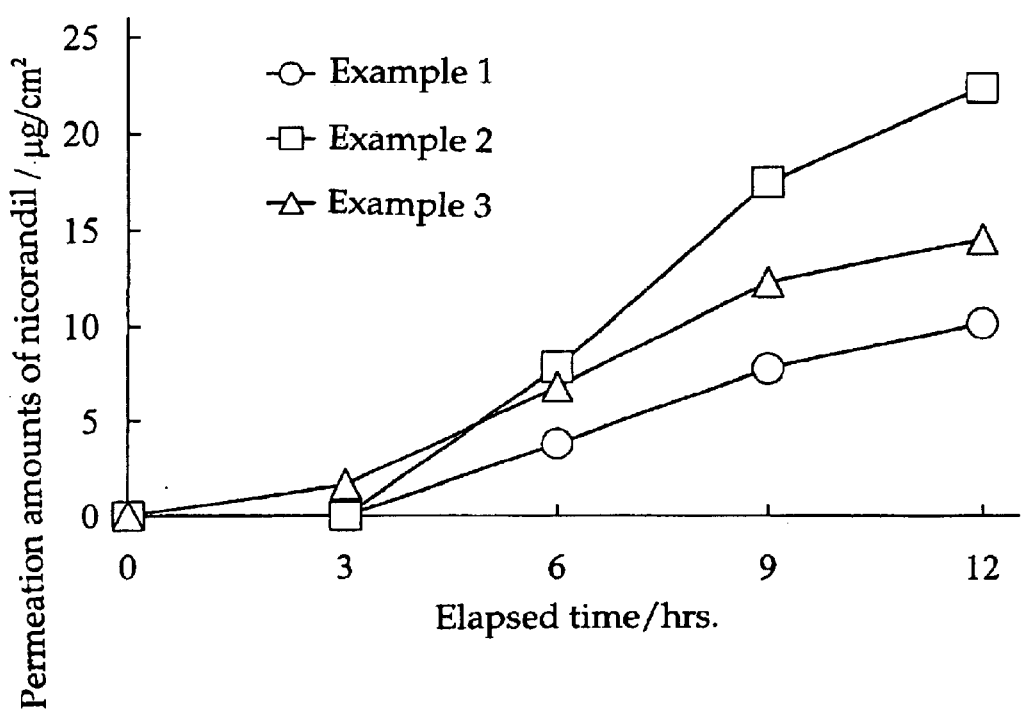
FIG. 2 is a chart showing the results of percutaneous absorption test of the percutaneous absorption preparation of the present invention.

A 8-week-aged male Wistar rat (body weight 170–190 g) was strangled, and the skin of its abdomen was taken out after removal of the hair with a hair clipper and a shaver. After the fat on the cutis side was removed with a forceps, the horny layer side, to which the percutaneous absorption preparations obtained in the above Examples 1–3 were attached, was applied to a vertical type diffusion cell (cell volume:4.0 ml, effective diffusion area: 0.95 cm$^2$) being kept in advance at 37° C. To the cutis side an isotonic phosphate buffer having a pH of 7.4 was applied, and the permeation experiment was conducted. During the experiment the starhead type stirring piece put in the cell of the cutis side was stirred by a magnetic stirrer. A predetermined amount of sample was taken with the lapse of time and added to acetonitrile containing an internal standard substance, and the medicine that had permeated was determined with a HPLC. FIG. 2 shows cumulative permeation amounts of the medicine at the times up to 12 hours from the beginning of the permeation test. In FIG. 2, the mark ○ indicates the results of Example 1, mark □ those of Example 2, and mark Δ those of Example 3.

All the publications, patents and patent applications cited herein are incorporated herein by reference in their entirety.

Industrial Applicability

The present invention can provide a percutaneous absorption preparation which is simple in its use and manufacturing method and which permits the medicine to be preserved stably at the time of preservation through controlling decomposition and deterioration of the medicine and which allows the medicine to move to the layer of adhesive and to be absorbed through the skin at the time of application of the preparation.

What is claimed is:

1. A composition comprising:

a supporting body, a solid medicine storage layer comprising one or more medicine(s) that permeate, dissolve, disperse or diffuse into a plasticized permeation controlling film which has been activated by moisture, a permeation controlling film, which is a water soluble polymer, that is plasticized when activated by moisture from the skin and that permits the permeation of the medicine(s) out of the medicine storage layer when plasticized, a layer of an adhesive comprising an acrylic adhesive and/or a rubber type adhesive, and a release liner, wherein said permeation controlling film comprises poly (vinyl alcohol) and said medicine is comprises nicorandil, dopamine hydrochloride or eperisone hydrochloride.

2. The composition according to claim 1 comprising a supporting body that has water-vapor permeability of 100 g/m$^2$ or less at the condition of 40° C. and 24 hours.

3. The composition according to claim 1 that comprises an adhesive that has water-vapor permeability of 100 g/m$^2$ or more at the condition of 40° C. and 20 hours.

4. The composition of claim 1 that comprises a medicine storage layer comprising one or more medicine(s) and one or more vehicle(s) or excipient(s).

5. The composition of claim 1 comprising one or more vehicle(s) or excipient(s) that are water-disintegrative substances.

6. The composition of claim 1 further comprising a medicine storage layer comprising one or more additive(s) or absorption accelerator(s), or both.

7. A method for administering one or more medicine(s) comprising applying the composition of claim 1 to the skin of a subject for a time and under conditions suitable for percutaneous absorption of said medicine(s).

8. A method for making the composition of claim 1 comprising:

attaching or laminating together;

a supporting body, a solid medicine storage layer comprising one or more percutaneously absorbable medicine(s) that permeate, dissolve, disperse or diffuse into a plasticized permeation controlling film which has been activated by moisture, wherein said medicine, is nicorandil, dopamine hydrochloride, or epirisone hydrocloride, a permeation controlling film that is plasticized when activated by moisture from the skin and that permits the permeation of the medicine(s) out of the medicine storage layer when plasticized wherein said permeation controlling film is poly(vinylalcohol), a layer of an adhesive and a release liner.

9. The composition according to claim 1 that comprises nicorandil.

10. The composition according to claim 1 that comprises dopamine hydrochloride.

11. The composition according to claim 1 that comprises eperisone hydrochloride.

* * * * *